United States Patent
Pilon-Clayton et al.

(10) Patent No.: US 11,690,893 B2
(45) Date of Patent: Jul. 4, 2023

(54) COMPOSITIONS AND METHODS OF USE FOR SECRETOGLOBINS TO PROTECT THE GLYCOCALYX VIA INTERACTIONS WITH HEPARAN SULFATE PROTEOGLYCAN PROTEINS

(71) Applicant: APC Research Assets LLC, Rockville, MD (US)

(72) Inventors: Aprile L Pilon-Clayton, Rockville, MD (US); Melissa E. Winn, Rockville, MD (US)

( * ) Notice: Subject to any disclaimer, the term of this patent is extended or adjusted under 35 U.S.C. 154(b) by 0 days.

(21) Appl. No.: 17/298,941

(22) PCT Filed: Dec. 2, 2019

(86) PCT No.: PCT/US2019/064068
§ 371 (c)(1),
(2) Date: Jun. 1, 2021

(87) PCT Pub. No.: WO2020/113232
PCT Pub. Date: Jun. 4, 2020

(65) Prior Publication Data
US 2022/0054587 A1   Feb. 24, 2022

Related U.S. Application Data

(60) Provisional application No. 62/925,058, filed on Oct. 23, 2019, provisional application No. 62/773,959, filed on Nov. 30, 2018.

(51) Int. Cl.
*A61K 38/17* (2006.01)
*A61K 47/61* (2017.01)
*A61K 47/54* (2017.01)
*A61P 37/06* (2006.01)

(52) U.S. Cl.
CPC ........ *A61K 38/1709* (2013.01); *A61K 47/543* (2017.08); *A61K 47/61* (2017.08); *A61P 37/06* (2018.01)

(58) Field of Classification Search
CPC ...... C07K 14/78; C07K 14/765; C07K 16/40; C07K 2319/74; C07K 2317/92; C07K 2317/94; C07K 2318/20; C07K 2319/31; C07K 14/76; A61P 3/06; A61K 38/00; A61K 39/39591; A61K 2039/505; A61K 2039/545
See application file for complete search history.

(56) References Cited

U.S. PATENT DOCUMENTS

| | | | |
|---|---|---|---|
| 7,329,638 B2 | 2/2008 | Yang et al. | |
| 7,846,899 B2 * | 12/2010 | Pilon | A61K 38/1709 514/1.5 |
| 8,470,767 B2 * | 6/2013 | Pilon | A61K 38/17 514/1.5 |
| 8,957,018 B2 * | 2/2015 | Pilon | A61P 11/00 435/375 |
| 9,394,349 B2 | 7/2016 | Pilon | |
| 2003/0109429 A1 * | 6/2003 | Pilon | A61P 37/02 514/1.5 |
| 2003/0207795 A1 * | 11/2003 | Pilon | C07K 14/4721 435/69.6 |
| 2006/0281681 A1 * | 12/2006 | Pilon | A61K 38/17 514/1.5 |
| 2011/0183887 A1 * | 7/2011 | Pilon | A61K 38/17 514/1.5 |
| 2015/0157689 A1 * | 6/2015 | Pilon | C07K 14/47 435/238 |
| 2016/0243193 A1 * | 8/2016 | Clayton-Pilon | A61P 11/00 |

FOREIGN PATENT DOCUMENTS

| | | |
|---|---|---|
| WO | 2008039941 A2 | 9/2008 |
| WO | 2011035140 A1 | 3/2011 |

OTHER PUBLICATIONS

Barker et al. Transplantation and inflammation: implications for the modification ofchemokine function. Immunology, vol. 143, pp. 138-145. (Year: 2014).*
Gunter, Jen. MD. The ongoing trauma of prematurity. NY Times. Published Apr. 15, 2020 Updated Apr. 20, 2020 Accessed online https://www.nytimes.com/2020/04/15/parenting/baby/prematurity-baby-burden.html. (Year: 2020).* WOISA, in PCT/US19/64068, dated Feb. 3, 2020.
Alphonsus CS et al: "The endothelial glycocalyx: a review of the vascular barrier", Anaesthesia, Blackwell Science LTD, GB, vol. 69, No. 7, Apr. 28, 2014 (Apr. 28, 2014), pp. 777-784, XP071067597, ISSN: 0003-2409, DOI: 10.1111/ANAE.12661.
Bernhard F Becker et al: "Degradation of 11-6 the endothelial glycocalyx in clinical settings: searching for the sheddases", British Journal of Clinical Pharmacology, Blackwell Scientific Publ, GB, vol. 80, No. 3, May 22, 2015 (May 22, 2015), pp. 389-402, XP071602312, ISSN: 0306-5251, DOI: 10.1111/BCP.12629.

(Continued)

*Primary Examiner* — Marcela M Cordero Garcia
(74) *Attorney, Agent, or Firm* — Cittone Demers & Arneri LLP; Henry J. Cittone

(57) ABSTRACT

SCGB-based preparations and methods to use these preparations to protect the glycocalyx in medical, veterinary, and cosmetic applications are provided. The secretoglobins (SCGBs) are a family of small secreted globular proteins present in all mammals and sharing conserved structure and thought to share similar immunomodulatory functions. Heparan sulfate proteoglycan proteins (HSPGs) are expressed on the outer membranes of cells and have carbohydrate side chains that, together, make up the glycocalyx. The glycocalyx is a protective layer surrounding all cells, acting as a filter regulating the passage of nutrients into the cell and modifying cell signaling by external factors. There are two major families of HSPGs including syndecans and glypicans, plus several other HSPGs in all mammals. SCGBs bind to, and interact with, HSPGs to further modulate cell signaling and cellular responses to external factors.

3 Claims, 6 Drawing Sheets

(56) References Cited

OTHER PUBLICATIONS

J.M. Tarbell et al: "The glycocalyx and its significance in human medicine", Journal of Internal Medicine, vol. 280, No. 1, Jan. 8, 2016 (Jan. 8, 2016), pp. 97-113, XP055713509, GB ISSN: 0954-6820, DOI: 10.1111/ioirn.12465.

Rehm Markus et al: "Shedding of the Endothelial Glycocalyx in Patients Undergoing Major Vascular Surgery With Global and Regional Ischemia", Circulation, vol. 116, No. 17, Oct. 23, 2007 (Oct. 23, 2007), pp. 1896-1906, XP055943377, us ISSN: 0009-7322, DOI: 10 1161/CIRCULATIONAHA.106.684852.

Martin Lukas et al: "The Endothelial Glycocalyx: New Diagnostic and Therapeutic Approaches in Sepsis", Biomed Research International, vol. 33, No. 22, Jan. 1, 2016 (Jan. 1, 2016), pp. 1-8, XP055835945, ISSN: 2314-6133, DOI: 10.1155/2016/3758278 Retrieved from the Internet:URL:http://downloads.hindawi.com/journals/ bmri/2016/3758278.pdf>.

Wang et al., Secretoglobin 3A2 Attenuates Lipopolsaccacharide-induced inflammation through inhibition of ERK and JNK Pahtways in Bronchial Epithelial Cells, Inflammation, vol. 38, No. 2 Apr. 2015, DOI: 10.1007/s10753-014-9992-0.

\* cited by examiner

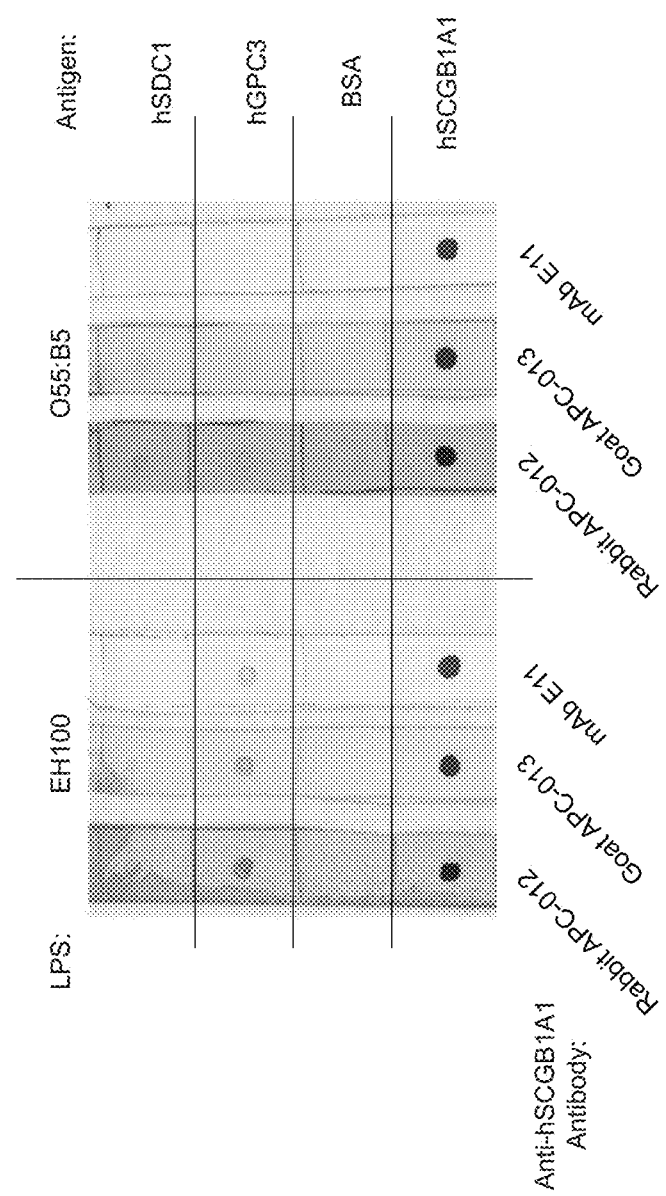

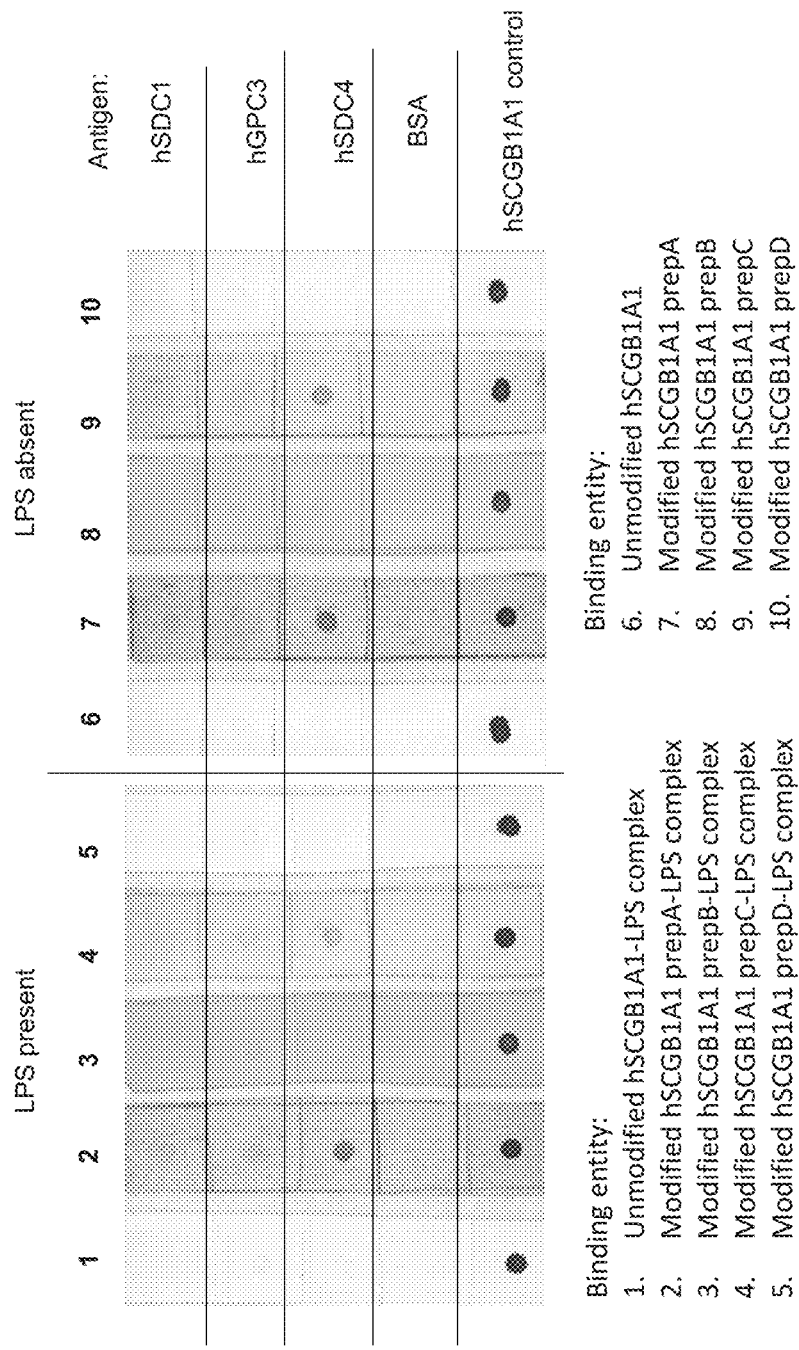

Western blot of DNPH-treated rhCC10 NaOCl reactions using anti-DNP antibody

| | | Amount loaded |
|---|---|---|
| 1. | Marker | |
| 2. | 50 ng MPO+ 50 eq $H_2O_2$ | 10 mcg |
| 3. | 2 eq mCPBA in water (0.5 mg/mL) | 10 mcg |
| 4. | 5 eq NaOCl in water (5.5 mg/mL) | 10 mcg |
| 5. | 5 eq NaOCl in water (1.4 mg/mL) | 5 mcg |
| 6. | 5 eq NaOCl in buffer (2.7 mg/mL) | 5 mcg |
| 7. | 5 eq NaOCl in buffer (0.7 mg/mL) | 5 mcg |
| 8. | rhCC10 | 5 mcg |

COMPOSITIONS AND METHODS OF USE FOR SECRETOGLOBINS TO PROTECT THE GLYCOCALYX VIA INTERACTIONS WITH HEPARAN SULFATE PROTEOGLYCAN PROTEINS

CROSS-REFERENCE TO RELATED APPLICATIONS

This application claims priority to and benefit of U.S. Provisional Patent Application 62/773,959, filed Nov. 30, 2018, currently pending and U.S. Provisional Patent Application 62/925,058, filed Oct. 23, 2019, currently pending, the disclosures of which are incorporated by reference herein in their entireties.

FIELD OF THE INVENTION

The invention relates to secretoglobins (SCGBs)-based compositions, preparations, and methods to use these preparations in medical, veterinary, and cosmetic applications. The secretoglobins (SCGBs) are a family of small secreted globular proteins present in all mammals and sharing conserved structure and thought to share similar immunomodulatory functions. SCGBs bind to, and interact with, heparan sulfate proteoglycan proteins (HSPGs), which are expressed on the outer membranes of cells, to modulate cell signaling and cellular responses to external factors.

BACKGROUND

The secretoglobins (SCGBs) are a family of small secreted globular multimeric proteins present in all mammals and sharing conserved structure and thought to share similar immunomodulatory functions (reviewed in Mukherjee, 2007). Heparan sulfate proteoglycans (HSPGs) are expressed on the outer membranes of cells and have carbohydrate side chains that together make up the glycocalyx, which is a protective layer that regulates penetration of fluids, ions, nutrients, signaling ligands, and other molecules into and between cells. Another name for HSPG carbohydrate side chains is glycosaminoglycans (GAGs), including heparan sulfate, chondroitin sulfate, and their derivatives. Syndecans and glypicans are the two main families of HSPGs. Syndecans have a transmembrane region that connects to the cytoskeletal matrix, facilitating formation of clathrin-coated pits and endosomes for transport of receptor-ligand complexes and uptake of other materials inside the cell. Syndecans may act as co-receptors to facilitate cell signaling by various ligands, such as growth factors, by loosely aggregating the ligands in their GAGs and bringing or holding them in closer proximity to their specific receptors. In contrast, glypicans do not span the membrane but are instead anchored in the membrane by glycerophosphoinositol and linked to the signal transduction apparatus of the plasma membrane. Glypicans also mediate a different type of cellular uptake via formation of lipid rafts. GAGs found in HSPGs include heparan sulfate and chondroitin sulfate, with minor carbohydrate variants present in different tissues. The degree of sulfation of GAGs is critical to their binding properties and thought to be an important regulator of homeostasis. Another major component of the glycocalyx of mammalian cells is hyaluronic acid (HA), which is not attached to any membrane-bound protein. All cells are normally surrounded by a glycocalyx, which may range in thickness from 20-2000 nm.

The precise composition of the glycocalyx, with respect to GAG and HA modifications, HSPG composition, and associated molecules, is not only specific to the cell of origin, but also to the organs and tissues in which it was synthesized. The glycocalyx of the epithelial cells lining the respiratory tract, the gastrointestinal tract, the urogenital tracts, mammary ducts, hair follicles, and the eyes, are major components of the mucosal layers of these systems and tissues, i.e. the epithelial glycocalyx (EpiG). There is a cellular glycocalyx surrounding circulating cells (red blood cells, white blood cells, platelets, fibroblasts) (CG) and a glycocalyx lining the lumen of the lymphatic system (LG). The endothelial glycocalyx (EG) of the circulatory system is maintained by vascular endothelial cells, lines the lumen of blood vessels, and is also specific to the organs and tissues in which it is localized, and is particularly important in regulating tissue penetration of circulating factors, acting much like a molecular sieve or filter, and in regulating cell adhesion. The EG is also a mechanosensor for shear stresses caused by local and systemic overpressure in blood vessels. In response to inflammatory signals, $O2/CO2$ imbalance, shear stresses, trauma, and other disruptions, the EG is shed by the action of matrix metalloproteases, heparanases, and other "sheddases" activated by damage or danger signals. Shedding of the EG results in exposure of the underlying vascular endothelial cells (VECs), and the junctions between VECs, to circulating fluids, proteins, and cells. This EG shedding enables cells and proteins to adhere to VECs and the endothelial lumen, including atherosclerotic plaque, platelets that form clots, and white blood cells such as neutrophils and monocytes, and fibroblasts, to migrate from the blood vessel into the tissues. Likewise, EG shedding results in leakage of serum fluid and plasma protein into tissues, resulting in edema that can be life-threatening in the lungs, heart, and other organs. EG shedding may also increase the risk of hemorrhage. SDC1 is a major component of the normal EG and circulating, "shed" SDC1 is recognized as a biomarker that increases markedly during EG shedding in life-threatening crises such as shock, trauma, and sepsis. Shed SDC1 also increases during cardiac surgery, lung resection, and acute lung injury. Thus, the EG has recently been recognized as a novel therapeutic target in critical care medicine; specifically, protection of the EG to maintain EG integrity during shock, sepsis, trauma, organ failure, pancreatitis, peritonitis, acute lung injury, and other systemic, life-threatening crises, etc., is needed.

The HSPGs expressed by immature and mature blood cells are also important in blood cell homing to various tissues, including lymph nodes, spleen, and thymus, as well as to damaged tissues, sites of injury and infection. They play a role in hematopoietic differentiation among cell lineages, as well as responses to specific insults and pathogens, including antigen uptake, sorting, processing, and presentation; and ultimately contribute to innate and adaptive immune responses. The HSPGs also play a role in solid tissue and organ development, angiogenesis, homeostasis, cellular proliferation, cancer and metastasis, and exosome formation and release, by originator cells and exosome uptake by other cells. Dysregulation of HSPG expression and/or inactivation of HSPGs via shedding often correlates with aggressive growth, tumor angiogenesis, and invasion of normal tissues by cancers such as lung, breast, colon, uterine, cervical, and other solid tumors, as well as hematological cancers (reviewed in Akl, 2015).

SUMMARY OF INVENTION

Aspects of the present invention relate to secretoglobins (SCGBs)-based compositions and preparations in medical, veterinary, and cosmetic applications.

Further aspects of the present invention relate to methods to use these preparations in medical, veterinary, and cosmetic applications.

In one aspect, a composition of a SCGB preparation consisting of a SCGB covalently linked to any type of lipid is provided. The composition may be one where the SCGB is SCGB1A1 and the lipid is LPS, Lipid A, a derivative of LPS or Lipid A, or a synthetic LPS or Lipid A. The composition may be one where the SCGB is SCGB1A1 and the lipid is dipalmitoyl phosphatidylcholine.

In another aspect, the SCGB is SCGB1D2 and the lipid is LPS.

In another aspect, the SCGB is SCGB1D4 and the lipid is LPS.

In yet other aspects the SCGB preparation is an SCGB in a non-covalent complex with any type of lipid.

In yet other aspects the SCGB preparation is an SCGB covalently linked to a glycosaminoglycan. The glycosaminoglycan may be heparin.

In yet other aspects the SCGB preparation is an SCGB in a non-covalent complex with a glycosaminoglycan. The glycosaminoglycan may be heparin.

In still further aspects, a method of use of an SCGB preparation to prevent shedding of the endothelial, epithelial, and/or lymphatic glycocalyx in a patient with distributive shock is provided.

In still further aspects, a method of use of an SCGB preparation to prevent shedding of the endothelial, epithelial, and/or lymphatic glycocalyx in a patient with cardiogenic shock is provided.

In still further aspects, a method of use of an SCGB preparation to prevent shedding of the endothelial, epithelial, and/or lymphatic glycocalyx in a patient with sepsis is provided.

In still further aspects, a method of use of an SCGB preparation to prevent shedding of the cellular, endothelial, epithelial, and/or lymphatic glycocalyx in a transplanted tissue or organ is provided.

In still further aspects, a method of use of an SCGB preparation to prevent shedding of the endothelial, epithelial, and/or lymphatic glycocalyx in a patient after a severe trauma is provided.

In still further aspects, a method of use of an SCGB preparation to prevent shedding of the endothelial, epithelial, and/or lymphatic glycocalyx in a patient during surgery is provided.

In still further aspects, a method of use of an SCGB preparation to induce cell death in a cancer cell is provided.

BRIEF DESCRIPTION OF THE DRAWINGS

FIGS. 3A-C: Far-Western blots illustrating binding of rhSCGB1A1 to recombinant human SDC1, SDC4, and GPC3 in the presence of two different types of LPS (EH100 and O55:B5). The SCGB1A1 bound to the HSPGs were detected with 3 different anti-human SCGB1A1 antibodies, including a rabbit polyclonal (APC-012), a goat polyclonal (APC-013), and a mouse monoclonal (E11). BSA was used as a negative control and rhSCGB1A1 was spotted onto the blots as a positive control. FIG. 3A shows rhSCGB1A1 binding to recombinant human SDC1 and GPC3 in the presence of 2 different types of bacterial endotoxin. FIG. 3B shows rhSCGB1A1 and rhSCGB3A2 binding to hSDC1, hSDC4, and hGPC3 in the presence and absence of LPS (EH100). FIG. 3C shows rhSCGB1A1 and ROS-modified rhSCGB1A1 binding to hSDC1, hSDC4, and hGPC3 in the presence and absence of LPS (EH100).

FIG. 4 depicts a Western Blot showing DNPH-treated rhCC10 NaOCl reactions using anti-DNP antibody. A 10-20% tricine SDS-PAGE gel was run on the modified rhCC10 preparations. NaOCl reaction products were run alongside MPO and mCPBA reaction products. The gel was blotted to PVDF then probed with rabbit polyclonal anti-DNP antibody (commercially available). Samples were not reduced but were mixed with SDS PAGE loading buffer and heated to 65° C. for 15 minutes prior to loading. Unmodified rhCC10 and MPO and mCPBA reaction products were not recognized by the anti-body under the conditions used. Only the NaOCl reaction products contained detectable DNP, indicating the presence of carbonyl groups in these preparations.

DETAILED DESCRIPTION

Figure 1:
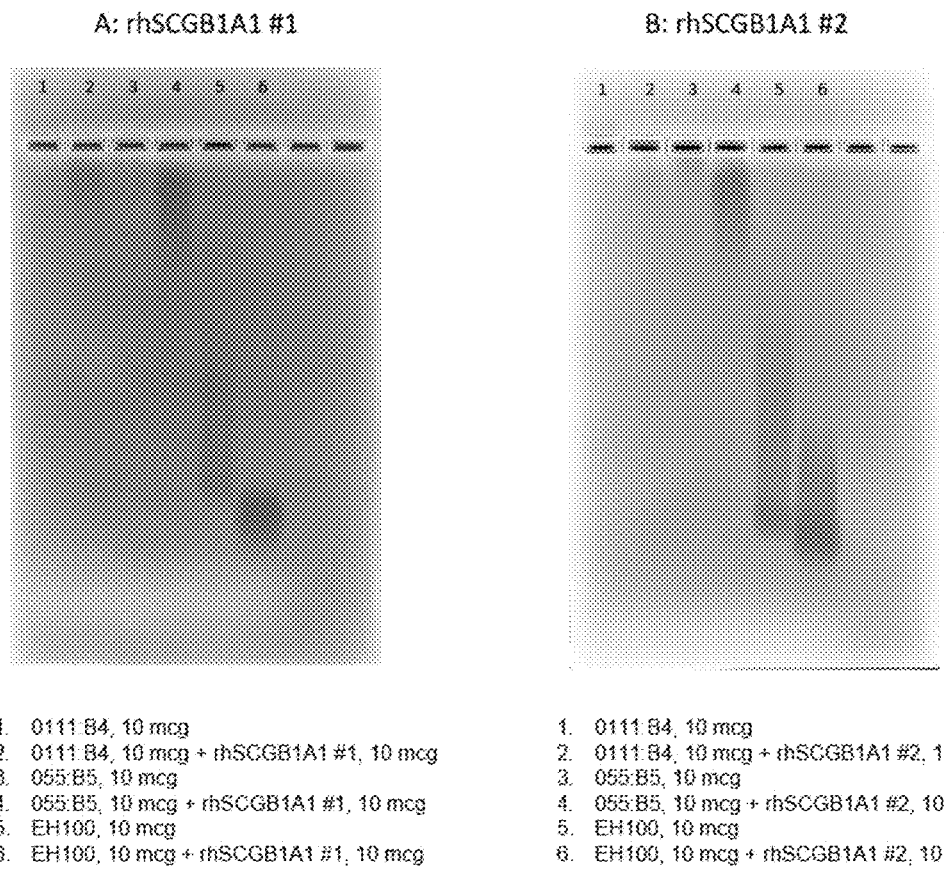
FIG. 1: Agarose gel electrophoretic mobility shift assay (EMSA) demonstrates non-covalently linked complexes between recombinant human SCGBs and LPS. Panels A and B show complexes between two different batches of rhSCGB1A1 and 3 types of LPS, including 0111:B4, O55:B5, and EH100.

The present invention is directed, inter alia, to provision of secretoglobins (SCGBs)-based compositions and preparations, capable of functioning in medicines, veterinary medicines, and cosmetics. And is directed to methods to use these preparations in medical, veterinary, and cosmetic applications.

Definitions

Active ingredient: Any component of a preparation or formulation of a product with a medical or veterinary application that mediates an intended pharmacologic effect on any molecular component, cell, tissue, organ, or system of the recipient. Examples of active ingredients include any glycosaminoglycans (i.e. heparin, heparan sulfate, chondroitin sulfate), linear or branched glycan, hyaluronic acid, aminoglycoside, signaling lectin (siglec), ganglioside, polysialic acid, or any derivatives thereof), any glycoprotein, any lipid, phospholipid, surfactant component, glycerophospholipid, glycolipid, sphingolipid, glycosphingolipid, arachidonic acid, eicosanoid, or analogue or derivative thereof, any polyamine or analogue thereof, any pH modifier, therapeutic nutrients, minerals, electrolytes, resuscitation fluids; drugs such as antivirals, antibiotics, statins, disease-modifying anti-rheumatic drugs, aspirin, NSAIDs, inflammatory bowel disease agents, metabolic bone disease agents, gastrointestinal agents, dental and oral treatment agents, genitourinary agents, cardiovascular agents, blood glucose regulators, CNS agents, analgesics, antidotes and antitoxins, antifungals, anti-inflammatory agents, antimigraine agents, antineoplastics, antiparasitics, anti-psychotic agents, antidepressants, anticonvulsants, antimycobacterials, antiemetics, anxiolytic agents, anti-infectives, antimyasthenic agents, anti-fibrotic agents, antidementia agents, anesthetics, antiparkinson agents, bipolar agents, dermatological agents, immunological agents, ophthalmic and otic agents, sedatives and hypnotics, hormones, hormone agents, hormone suppressants, or analogues thereof, antihistamines, bronchodilators, muscle relaxants, vasodilators, vasosuppressors, biologics, recombinant human proteins, a second SCGB, enzyme replacement therapies, monoclonal antibodies, blood products, exosomes, micelles, liposomes, and other vesicle preparations (whether derived from live cells on not), vaccines, and live cells, including stem cells, platelets, red blood cells, unmodified white blood cells, and white blood cells engineered or differentiated in vitro and infused into a patient.

SCGB1A1 preparation: A preparation of synthetic SCGB1A1, a modified SCGB1A1, or SCGB1A1 analogue or derivative, alone or in combination with a second active ingredient that may be covalently attached or non-covalently attached to the SCGB1A1, such second active ingredient modifying the binding activity of the SCGB1A1 to HSPGs, HSPG proteins, glycocalyx components, receptors, or other cell surface determinant.

SCGB preparation: A preparation of one or more synthetic SCGBs, one or more modified SCGBs, or one or more SCGB analogues or derivatives, alone or in combination with a second active ingredient that may be covalently attached or non-covalently attached to the SCGB, such second active ingredient modifying the binding activity of the SCGB to HSPGs, HSPG proteins, glycocalyx components, receptors, or other cell surface determinant.

Modified SCGB: A preparation of a synthetic SCGB that is modified according to methods and compositions as described in U.S. Ser. No. 15/212,277 (enclosed herein.)

SCGB complex: Any covalently linked complex of a SCGB, modified SCGB, or SCGB analogue or derivative with another molecule or active ingredient.

Shock: The lack of sufficient blood flow to body tissues. There are four major types of shock based on the underlying cause as shown in Table 1.

TABLE 1

| Type | Cause |
|---|---|
| Low volume | Blood loss, vomiting, pancreatitis |
| Cardiogenic | Heart attack, cardiac bruising |
| Obstructive | Cardiac tamponade, pulmonary embolism, tension pneumothorax |
| Distributive | Sepsis, anaphylaxis, endocrine (adrenal insufficiency resulting in deficiency of steroid hormones (cortisol)), spinal cord injury, overdose |

Secretoglobins (SCGBs): A family of small, globular secreted proteins that share a common monomer tertiary structure consisting of four alpha helices, called a four helical bundle, that form homo- and/or heterodimers, and other multimers. SCGBs are present in all mammals and are thought to share similar immunomodulatory functions.

Heparan Sulfate Proteoglycans (HSPGs): Cell surface proteins that bear heparan sulfate and chondroitin sulfate carbohydrate side chains. Syndecans and glypicans are the two major protein families that make up the HSPGs.

Glycosaminoglycans (GAGs): A group of long unbranched carbohydrates/polysaccharides consisting of keratin sulfate, hyaluronic acid, heparan sulfate, and chondroitin sulfate.

Hyaluronic Acid (HA): An anionic, non-sulfated GAG and major component of cellular glycocalyx, EpiG, EG, and extracellular matrix; and widely distributed throughout all tissues and organs of the body in humans and other mammals with numerous functions in controlling the viscosity of various body fluids, cell proliferation and migration, extracellular matrix interactions, granulation, and wound repair.

Epithelial Glycocalyx (EpiG): The glycocalyx is a protective layer that regulates penetration of fluids, ions, nutrients, signaling ligands, and other molecules into and between cells composed of HSPGs and HA. In the context of this specification, the epithelial glycocalyx refers to the glycocalyx of the epithelial cells lining the respiratory tract, the gastrointestinal tract, the urogenital tracts, mammary ducts, hair follicles, and the eyes, which are continuous and are major components of the mucosal layers of these systems and tissues.

Circulating Cells (red blood cells, white blood cells, platelets, fibroblasts): Living cells that circulate in the blood of a mammal.

Cellular glycocalyx (CG): Every cell has its own glycocalyx, including circulating cells such as red blood cells, white blood cells, platelets, and fibroblasts. The cellular glycocalyx is a protective layer that regulates penetration of fluids, ions, nutrients, signaling ligands, and other molecules into cells composed of HSPGs and HA.

Glycocalyx Lining The Lumen Of The Lymphatic System (LG): In the context of this specification, the lymphatic glycocalyx (LG) refers to the glycocalyx of the cells lining the lymphatic vessels between organs, tissues, and lymph nodes and through which mature and immature white cells travel during the adaptive immune response.

Endothelial Glycocalyx (EG): The endothelial is produced and maintained by vascular endothelial cells, lines the lumen of blood vessels throughout the body, and is particularly important in regulating tissue penetration of circulating factors, acting much like a molecular sieve or filter, and in regulating cell adhesion and sensing mechanical stress.

Vascular Endothelial Cells (VECs): The single layer of squamous cells that line the lumen of the blood vessels from the heart to peripheral capillaries, produce and maintain the endothelial glycocalyx, and are in direct contact with blood.

Syndecan-1 (SDC1): A transmembrane protein found in humans and other mammals that is encoded by the sdc1 gene and expressed in many cell types. It resides in the plasma membrane, with an extracellular domain that bears heparan sulfate and chondroitin sulfate side chains and has highly conserved membrane spanning and cytoplasmic domains. It mediates cell binding, cell signaling, cytoskeletal organization, cell interactions with the extracellular matrix, endocytosis, intracellular sorting of endosomes, and exocytosis.

Lipopolysaccharide (LPS): Also known as endotoxin, LPS is a highly inflammatory and immunogenic complex made of of carbohydrate (polysaccharide) and lipid components, often accompanied by protein components as well, derived from Gram negative bacteria. LPS can be quite heterogeneous with numerous variations in the lipid and carbohydrate components.

Lipid A: A component of LPS that anchors it to the bacterial outer membrane in bacteria. It is a danger signal to the mammalian immune system and is highly inflammatory. Lipid A consists of two carbohydrate (glucosamine) units with attached acyl (lipid) chains and typically contains a phosphate group on each carbohydrate.

Acute Respiratory Distress Syndrome (ARDS): The most severe type of respiratory failure in which the ratio of the percent of arterial oxygen over the percent (fraction) in inspired oxygen is less than 300 mm Hg (mm of mercury; a pressure measurement) and accompanied by severe widespread inflammation in the lungs.

Antigen Presenting Cells (APCs): Any cell that takes up an antigen and sorts and processes it internally, then presents or displays the processed antigen on its surface in conjunction with co-stimulatory surface molecules to elicit an antigen-specific response in a recipient cell. Typically, recipient cells that develop antigen-specific responses are T cells and B cells; and APCs are usually dendritic cells but several other types of APCs have been observed.

Electrophoretic Mobility Shift Assay (EMSA): Electrophoresis is a biochemical method in which complex, large biomolecules are spread out according to their size and degree of net negative or positive surface charge within a solid hydrogel support such as agarose or polyacrylamide. EMSA involves a technique in which two biomolecules are combined to form a complex before being loaded into the gel support. If the two biomolecules form a stable complex, then the size and surface charge of the complex is altered compared to the two individual molecules, resulting in a different migration pattern of the complex through the gel, aka a mobility shift.

Synthetic Human SCGB3A2 (rhSCGB3A2): An artificial, man-made version of the human SCGB3A2 protein, which may be produced synthetically using recombinant or chemical methods, or a combination of the two, and having the same or similar properties as the native human SCGB3A2 protein.

Rabbit Polyclonal (APC-012): A polyclonal IgG antibody produced in rabbits using standard immunization methods. In the context of this specification the antigen used to generate the APC-012 antibody was recombinant human SCGB1A1 protein.

Goat Polyclonal (APC-013): A polyclonal IgG antibody produced in goats using standard immunization methods. In the context of this specification the antigen used to generate the APC-013 antibody was recombinant human SCGB1A1 protein.

Mouse Monoclonal (E11): A monoclonal antibody produced in mouse cells using standard immunization and hybridoma methods and that is commercially available (Santa Cruz Biotechnology, San Diego, Calif.). In the context of this specification the antigen used to generate the E11 antibody was a chemically synthesized portion of the human SCGB1A1 protein.

Glypican-3 (GPC3): A cell surface membrane protein found in humans and other mammals that is encoded by the gpc3 gene and expressed in many cell types, mostly of fetal or cancerous origin. It resides in the plasma membrane, with an extracellular domain that bears heparan sulfate and chondroitin sulfate side chains and anchored in the plasma membrane via glycosyl phosphatidylinositol linkage. Glypicans play a role in cell signaling, growth, and division via the Wnt pathway, and in uptake of environmental material via lipid rafts.

Cultured Human Cells (HEK293): An immortal cell line derived from human embryonic kidney cells that is commonly used for experiments involving expression of non-native proteins and production of foreign proteins.

Dipalmitoyl Phosphatidylcholine (DPPC): A type of phospholipid that is a major component of mammalian cell membranes and lung surfactant. DPPC is a substrate for phospholipase A2.

Syndecan-4 (SDC4): A transmembrane protein found in humans and other mammals that is encoded by the sdc4 gene and expressed in many cell types. It resides in the plasma membrane, with an extracellular domain that bears heparan sulfate and chondroitin sulfate side chains and has highly conserved membrane spanning and cytoplasmic domains. It mediates cell binding, cell signaling, cytoskeletal organization, cell interactions with the extracellular matrix, endocytosis, intracellular sorting of endosomes, and exocytosis.

mCPBA: meta-choloroperbenzoic acid: A mild chemical oxidizing agent.

NaOCl: sodium hypochlorite: A harsh chemical oxidizing agent.

Based on the discovery described herein that a SCGB preparation binds to at least two different HSPGs, we prove that SCGB preparations bind to HSPGs in the CG or EG. These binding interactions between SCGB preparations and HSPGs are at least partially dependent on the presence of a lipid moiety, such as LPS. We believe that the composition of any tissue or organ CG, EpiG, LG, or EG will include locally-produced SCGB, with or without some amount of SCGB1A1. Considering the biological activities of SCGB1A1 and SCGB3A2 in combination with the discovery of SCGB-HSPG interactions, we synthesized SCGB preparations that protect the CG, EpiG, LG, and EG by preventing cleavage of either or both the protein or GAG components of the HSPGs, thereby preventing local shedding of the EG and minimizing vascular permeability.

Shock: High dose SCGB1A1 is known to inhibit increased vascular permeability during acute inflammatory responses, however, the mechanism of this effect was not understood until the interaction of a SCGB1A1 preparation with HSPGs was uncovered. Due to the varied types of shock and the critical nature of the condition, the types of shock to which SCGB1A1 could be safely and efficaciously applied have not been obvious in the past. The identification of HSPGs as binding partners for SCGB1A1 and/or SCGB preparations in the EG, LG, and EpiG, with a major mechanism of action being protection of the EG, LG, and EpiG, now points to and enables the application of SCGB1A1 and/or SCGB preparations in distributive, obstructive, and cardiogenic shock, as well as pancreatitis but not in low volume shock due to blood loss or vomiting.

Infection: HSPGs in EpiG and EG of different tissues are often involved in initiation of bacterial, fungal, viral, mycobacterial, parasitic, and other types of infections by facilitating receptor binding, cellular adhesion, and/or cellular uptake of the infectious agent. SCGB preparations binding to HSPGs block the interactions of many infectious agents with their cellular receptors, including HSPGs, and/or cellular uptake that requires syndecan, glypican, or HSPG function.

Transplantation: Organs and tissues that are typically transplanted into human or mammalian recipients include, but are not limited to heart, lung, kidney, liver, limb (hand, finger, arm, foot, etc.), eye, ear, face, skin and cultured skin, uterus, bladder and cultured bladder, bone marrow, platelets, red blood cells, and whole blood, or any other organ or tissue intended for transplant. The numbers of transplants performed is increasing over time and the types of tissue transplants is becoming more diversified as surgical methods and tissue matching improves, as well as increasing numbers of transplant donors and culture organs. Organs and tissues, whether human or animal or hybrid in origin, that are removed from the donor or culture prior to transplantation into a recipient deemed to be in need of organ replacement typically undergo a period of oxygen deprivation and CO2 buildup while unconnected to the circulatory system of the donor and recipient, or between the tissue culture and recipient. This period of oxygen deprivation followed by re-connection to an oxygen source causes ischemia-reperfusion injury. In addition, solid organs or tissues also undergo shear stresses from the severing of blood vessels and surrounding tissues required to physically separate the transplant from the donor and subsequent physical trauma associated with handling.

The EG senses and responds to both O2/CO2 imbalances and shear stresses, resulting in EG shedding from the transplant. The shedding of the EG, and possibly the EpiG and LG, during and following surgeries and trauma, as measured by increases in circulating shed SDC1, is well documented. Transplanted organs that have lost a significant proportion of their EG are more susceptible to adherence and infiltration at the site of shedding by neutrophils, monocytes, and fibroblasts from the recipient, that we believe facilitates primary graft dysfunction, and acute and chronic rejection of the transplanted tissue. Likewise, the removal of a defective organ from the recipient causes shear stresses in the severed blood vessels for that organ, which are then clamped off to prevent catastrophic blood loss during the transfer. Further shear stress and trauma to major blood vessels in the donor organ and the recipient results from the suturing of blood vessels during the attachment of the donor organ to the recipient's circulatory system, likely resulting in further shedding.

Similarly, non-solid cellular transplants such as bone marrow, platelets, red blood cells, whole blood, and stem cells may also undergo shear stresses during collection, manipulation, transport, and infusion that can damage or cause shedding of the individual cellular glycocalyx (CG). The loss of the cellular glycocalyx may not only compromise the function and responses of cellular transplants, but also facilitate rejection by exposing cell surface determinants that are not included in the range of antigenic determinants used to match donors and recipients.

The identification of HSPGs as binding partners for SCGB1A1 and/or SCGB preparations in the EG, EpiG, LG, and CG now points to the application of SCGB1A1 and/or SCGB preparations in transplantation of solid tissues and organs, as well as hematopoietic cells and stem cells, through preservation and protection of the EG, EpiG, LG, and CG.

Cancer (solid tumors): HSPG expression is often dysregulated in different solid tumors and shed HSPGs in the circulation are diagnostic of late stage solid tumors and/or metastases, as well as more aggressive, faster-growing and invasive tumors. Examples 1-3 show that SCGB1A1 forms a complex with LPS, and LPS+heparin, and can bind to SDC1 and SDC4, as well as glypican-3 (GPC3). SCGB1A1 preparations and other SCGB preparations interact with syndecans, and possibly other HSPGs, on the surfaces of solid tumor cells and trigger cell death in tumor cells. Solid tumors that could be eliminated by SCGB-HSPG-mediated cell death include, but are not limited to, lung, liver, colorectal, gastric (stomach), pancreatic, vascular endothelial, thyroid, bladder, thymus, intestinal, esophageal, breast, prostate, endometrial, cervical, oral, nasopharyngeal, neuronal, and brain.

Hematologic cancers: HSPG expression is often dysregulated in different hematologic cancers and shed HSPGs in the circulation are diagnostic of malignantly transformed white or red blood cells, as well as more aggressive, faster-growing malignancies. Examples 1-3 show that SCGB1A1 forms a complex with LPS and can bind to SDC1 and SDC4, as well as GPC3. SCGB1A1 preparations and other SCGB preparations interact with syndecans, and possibly other HSPGs, on the surfaces of hematologic cancer cells and trigger cell death in hematologic cancer cells.

EXAMPLES

Example 1: Binding of human SCGB1A1 to bacterial lipopolysaccharide (LPS), also known as endotoxin. LPS is made up of lipid, carbohydrate chains (polysaccharide), and a small amount of protein derived from bacterial cell membranes. LPS is an extremely potent inflammatory mediator and must be specifically reduced to a very low or undetectable level in medicinal preparations in order to minimize toxicity. We observed that synthetic human SCGB1A1 (rhSCGB1A1) binds to LPS using an electrophoretic mobility shift assay (EMSA) in which the migration of LPS through an agarose gel was accelerated in the presence of SCGB1A1 as shown in FIG. 1. The agarose gel EMSA of FIG. 1 demonstrates the formation of non-covalently linked complexes between recombinant human SCGB1A1 and LPS. Panels A and B show complexes between two different batches of rhSCGB1A1 and 3 types of LPS, including 0111:B4, O55:B5, and EH100. Briefly, the EMSA method used 10 micrograms (mcg) of three different preparations of LPS dissolved in ultrapure water and incubated with and without rhSCGB1A1 at 37° C. for 30 minutes. The samples were mixed with loading buffer then loaded onto a 0.8% Tris-acetate-EDTA agarose gel and electrophoresed at 100V until the dye front reached the bottom of the gel. The gel was washed in ultrapure water and immersed in 0.2 M imidazole for 20 minutes with gentle agitation. The gel was washed again in ultrapure water then incubated in 0.2 M zinc sulfate for several minutes until bands became visible. The gel was washed again in ultrapure water to stop the staining and scanned with a densitometer.

Figure 2:
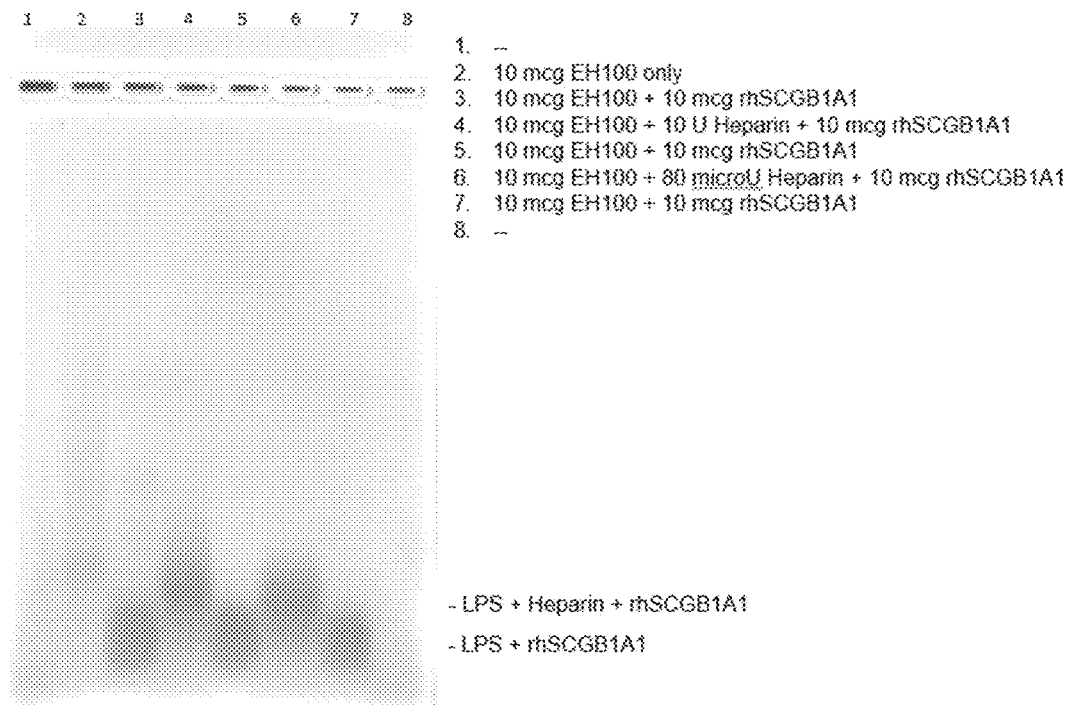
FIG. 2: Agarose gel EMSA demonstrates non-covalently linked 3-way complexes between rhSCGB1A1 and LPS EH100 and heparin. The order in which each component was added is indicated by the order in which the components are listed for each lane.

Example 2: Detection of complex between SCGB, LPS, and heparin. The SCGB1A1-LPS complex also binds to carbohydrate side chains and we used the EMSA to show this. FIG. 2 shows that the addition of heparin, a low molecular weight preparation of HSPG protein side chains derived from porcine intestines and used medically as an anticoagulant, shifts the SCGB1A1-LPS complex, creating a SCGB1A1-LPS-heparin complex. This 3-component complex is formed regardless of the order in which the components are added to the mixture. This discovery demonstrates that SCGB1A1 can form a 3-way complex with LPS and a HSPG side chain and we infer that the property of forming a 3-way complex among these components is conserved among different SCGBs. We further infer from this that SCGB1A1 and other SCGBs can also interact directly with the heparan sulfate and chondroitin sulfate side chains of HSPGs.

Example 3: Binding of SCGB1A1-LPS complexes to HSPGs in vitro, binding of multiple SCGBs binding to multiple HSPGs in the presence and absence of LPS, and binding of chemically modified rhSCGB1A1 to HSPGs. Recombinant human syndecan-1 (hSDC1), syndecan-4 (hSDC4), and glypican-3 (hGPC3), all expressed in cultured human cells (HEK293) in order to best approximate human HSPG protein side chains in humans in vivo, were purchased from a commercial vendor. The binding of the rhSCGB1A1-LPS complexes to these two HSPG proteins was investigated using a "Far Western" dot blot method. Briefly, 200 ng each of SDC1, SDC4, GPC3, rhSCGB1A1 (positive control), and bovine serum albumin (BSA; a negative control), all in phosphate buffered saline (PBS) pH 7.4, were spotted onto nitrocellulose membranes and allowed to dry. The membranes were blocked in 5% non-fat dry milk in PBS pH 7.4 for 1 hour at room temperature. The rhSCGB1A1-LPS complexes were prepared as in Example 1 (1:1 weight ratio) during the blocking step. After blocking, the membranes were equilibrated in citrate buffer, pH 6.5, then the rhSCGB1A1-LPS complexes were diluted in citrate buffer, pH 6.5 to 50 mcg/ml each of rhSCGB1A1 and LPS, added to the blocked membrane, and incubated overnight at 4° C. with gentle agitation. The membrane was washed with PBS pH 7.4, 0.1% Tween-20 (PBS-T) and incubated in the primary anti-hSCGB1A1 antibody. Three different antibodies were tested, including a rabbit polyclonal, a goat polyclonal, and a mouse monoclonal antibody, all raised against SCGB1A1 as the antigen, as shown in FIG. 3A. Each antibody was diluted 1:1,000 in 0.1% non-fat dried milk in PBS-T and incubated with the blot for 1 hour at room temperature with gentle agitation. The membranes were washed with PBS-T and incubated in secondary antibody, which were each conjugated to alkaline phosphatase enzyme, diluted 1:8,000 in 0.1% non-fat dried milk in PBS-T, and incubated with the membranes for 1 hour at room temperature. The membranes were washed with PBS-T then incubated in NBT/BCIP to develop color.

Figure 3B:
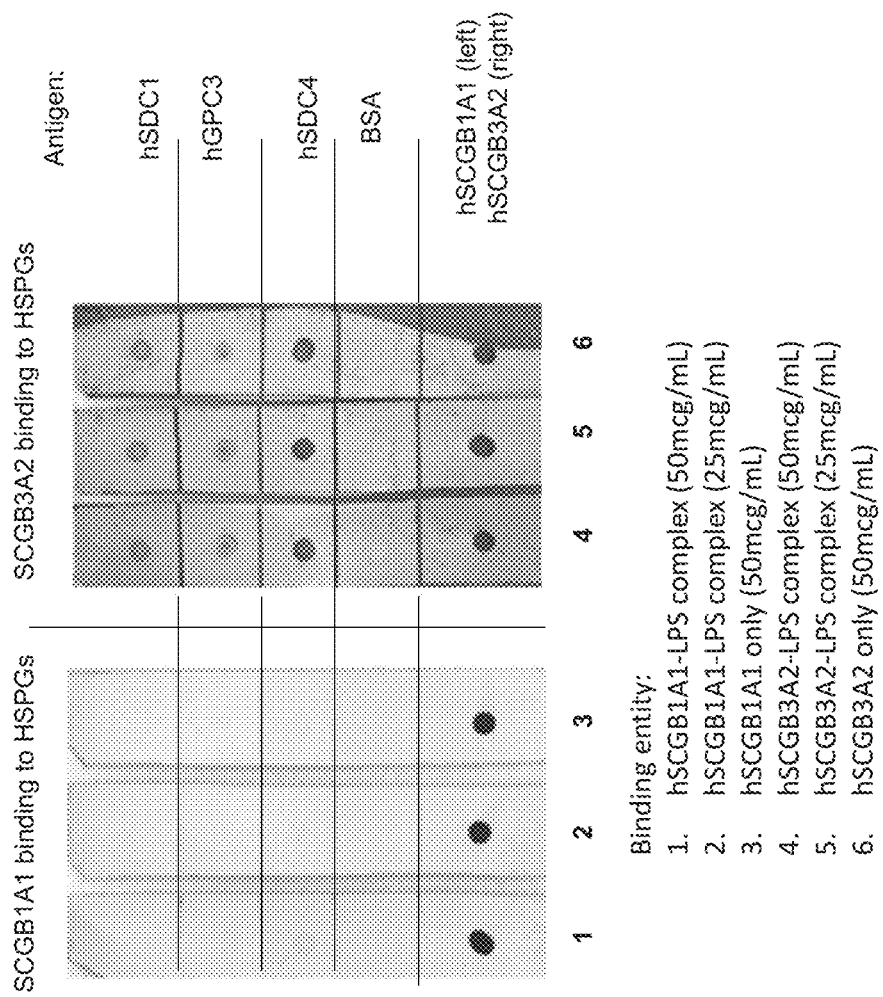
Figure 6:
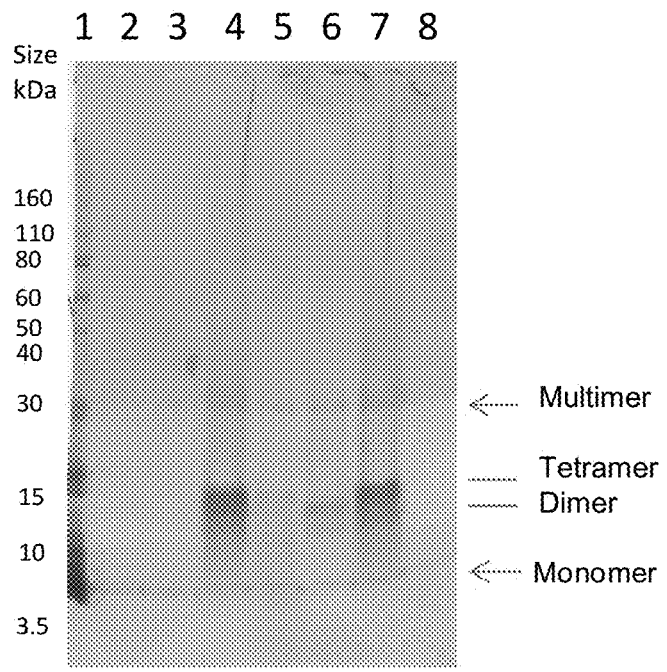

FIGS. 3A-C show the results of these experiments. In FIG. 3A, all three antibodies showed rhSCGB1A1-LPS complexes bound to both hSDC1 and hGPC3. However, the reaction was much stronger for LPS EH100 than for O55:B5, and for hGPC3 compared to hSDC1, with the rabbit polyclonal antibody providing the strongest signal. Thus, the 3 component complexes are formed regardless of which type of LPS and which HSPG protein was used. This discovery demonstrates that SCGB1A1 also forms a 3-way complex with LPS and a HSPG protein and we infer that the property of forming a 3-way complex among these components is conserved among different SCGBs.

FIG. 3B shows that both rhSCGB1A1 and rhSCGB3A2 bind to human hSDC4 and hGPC3 in the presence or absence of LPS using this method with rabbit polyclonal antibodies raised against rhSCGB1A1 and rhSCGB3A2, respectively. Despite the positive binding results shown in FIG. 3A, the rhSCGB1A1 did not demonstrate clear binding to hSDC1 in this experiment, suggesting that the interaction between rhSCGB1A1 and hSDC1 is relatively weak compared to hSDC4 and hGPC3, and compared to rhSCGB3A2. The rhSCGB3A2 showed clear binding to hSDC1, with and without LPS present. The rhSCGB1A1 bound to hSDC4 most strongly, as did rhSCGB3A2. The rhSCGB3A2 bound to all 3 HSPGs more strongly than rhSCGB1A1 with binding to hGPC3 being the weakest interaction. The SCGB-HSPG interactions did not require the presence of LPS in this assay format, since both proteins bound to HSPGs in the absence of LPS. SDC4 is widely expressed in many tissues, including vascular endothelial cells, lung, and white blood cells.

FIG. 3C shows the effect of ROS-modification of rhSCGB1A1 on binding to HSPGs in vitro. Modification of rhSCGB1A1 by reaction with reactive oxygen species (ROS) enhances binding to HSPGs in vitro, with or without LPS, as shown in FIG. 3C. The rhSCGB1A1 was reacted with different chemicals to induce ROS modification, then incubated with or without LPS, then were added to the dot blots and detected by rabbit polyclonal anti-rhSCGB1A1. Reactions to generate PrepsA-D in FIG. 3C were as follows:

TABLE 2

| Sample ID | ROS modifier | Molar Ratio (rhSCGB1A1: # oxidizing equivalents) | Degree oxidation (anti-DNP reactivity) |
|---|---|---|---|
| PrepA | NaOCl | 1:15 | Severe (DNP+) |
| PrepB | mCPBA | 1:10 | Mild (DNP−) |
| PrepC | Peroxynitrite | 1:10 | Mild (DNP−) |
| PrepD | NaOCl | 1:1 | Mild (DNP−) |

FIG. 3C shows the different preparations of rhSCGB1A1 modified by exposure to reactive oxygen species (ROS) generated by different chemical oxidants result in varying patterns of HSPG binding and the degree of oxidation is shown by binding to dinitrophenol (DNP) in Western blots. The extent of the chemical reaction and modification of rhCC10 can be estimated by the detection of reactive carbonyl groups. The presence of carbonyl groups in ROS reacted rhCC10 samples can be detected by labeling the carbonyl groups with 2,4-dinitrophenylhydrazine (DNPH), which adds a dinitrophenylhydrazone group (DNP), then analyzing the reaction products by Western blot using anti-DNP antibody as shown in FIG. 4. There is a baseline signal for monomer and tetramer in the unmodified CC10 (lane 8) which is exceeded in all other samples, regardless of type of ROS used in the reaction. Therefore, all ROS reactions produced some species that contained carbonyl groups. The unmodified dimer, and dimer in MPO and mCPBA modified preps show no reactivity and even blocked the background (see 'ghost bands' at dimer position in lanes 2, 3, and 8.) There appears to be a combination effect of rhCC10 concentration and buffer in the NaOCl reaction. The signal strength in lane 4 is over 10× greater than lane 5, which is more than expected by the 2× difference in protein present. This Suggests that higher rhCC10 concentration provides for a more extensive reaction than lower concentration when the reaction is done in water. The signal strength in lanes 4 and 7 is equal, despite that lane 7 contains half the protein, indicating that the reaction is more efficient in 10 mM phosphate buffer, pH 7.4 than in water. The signal strength in lane 6 is much less than in lane 7, despite that the same amount of protein is present. These observations indicate that the NaOCl reaction was more efficient when rhCC10 concentration is lower in the presence of buffer. Therefore, effect of rhCC10 concentration on reaction efficiency is opposite in water versus buffer. These differences illustrate how the process for chemical modification of rhCC10 with NaOCl is optimized. For example, an optimized process for NaOCl-mediated chemical modification of CC10 would involve the use of a lower concentration of rhCC10, in the presence of a low strength phosphate buffer at neutral pH.

Notably rhSCGB1A1 modified by NaOCl (1:15 molar ratio) and peroxynitrite bind most tightly to hSDC4 compared to unmodified and the mCPBA or NaOCl (1:1) reaction products, while binding of all ROS-modified and unmodified rhSCGB1A1 to hGPC3 is roughly equivalent. The presence or absence of LPS (EH100) did not impact binding of any of the rhSCGB1A1 preparations to HSPGs in this experiment, except that binding of peroxynitrite-reacted rhSCGB1A1 (prepC) to hSDC1 was stronger in the presence of LPS. Binding to hSDC1 and hSDC4 was stronger in rhSCGB1A1 preparations with more extensive ROS-mediated chemical modifications. These results illustrate that chemical modifications to rhSCGB1A1 modulate HSPG binding and the strength of HSPG-SCGB interactions.

Example 4: SCGBs bind to lipids, phospholipids, other lipids. The EMSA method of Example 1 is used to demonstrate binding of SCGB1A1 to one or more selected from among a lipid, phospholipid, surfactant component (dipalmitoyl phosphatidylcholine (DPPC), also known as lecithin, or dipalmitoyl phosphatidylethanolamine), glycerophospholipid, glycolipid, sphingolipid, or glycosphingolipid, in the absence of added calcium. An alternate method to detect SCGB-lipid binding is thin layer chromatography in which spots corresponding to the lipid migrate to different positions in the presence of an SCGB, as described in Mantile et al. (1993). Briefly, photo-activatable lipids and lipid analogues are incubated with SCGBs, then cross-linked by ultraviolet or other light exposure. Lipid controls and mixtures containing complexes of SCGBs with lipid moieties are then spotted onto pre-channeled Silica Gel G TLC plates and placed in TLC chambers with petroleum ether/diethyl ether/acetic acid (70:30:1) eluent. Lipids are stained with iodine vapor and migration of the lipid spots with and without SCGB are compared. This illustrates that one method of synthesizing SCGB preparations of the invention is the use of photo-activatable lipids, lipid analogues, and other compounds to generate covalently linked SCGB complexes that can interact with HSPGs to mediate therapeutic effects.

Example 5: Prevention and Treatment of Distributive Shock. The SCGB1A1 therapeutic preparation may consist of: 1) rhSCGB1A1 alone, 2) a non-covalent complex or nanoparticle containing rhSCGB1A1 and LPS or other lipid species as described in Example 4; or 3) a mixture containing SCGB1A1 covalently linked to LPS (PubChem CID 11970143 ($C_{205}H_{366}N_3O_{117}P_5$; 4.899 kg/mol; InChI Key: YPXVSQSYDIMPDZ-AUUHBOKRSA-N)), to a LPS species such as Monophosphoryl Lipid A (MPLA; such as Compound CID: 136212441 ($C_{54}H_{106}N_3O_{17}P$; 1100.4 g/mol; InChIKey: WBMOMCHVNLUEBA-UPPR-WESDSA-N) called Monophosphoryl Tri-Acyl Lipid A (3A-MPLA)), or to another lipid species as described in Example 4. Covalent linkage may be achieved by a physical method such as heating to 65° C. for 30 minutes, by chemical method linking sulfhydryl or amine group on the LPS species to an amine or sulfhydryl group on the protein, respectively, using established chemistries; or by enzymatic method such as transglutaminase-mediated cross-linking of a LPS species to a protein. The dose of the SCGB1A1 preparation is administered intravenously to a septic patient to prevent or treat distributive shock is between 20 ng/kg and 20 mg/kg, more specifically 1-20 mg/kg/day, for up to 7 consecutive days. The SCGB1A1 preparation binds to SDC1, SDC4, GPC3, or other HSPG located in the EG, blocking degradation and shedding of the SDC1, SDC4, GPC3, or other HSPG component from the EG. The maintenance of the integrity of the EG minimizes the increase in vascular permeability due to sepsis, enabling the patient to survive the episode.

Example 6: Prevention of EG, EpiG, and/or LG shedding in an organ transplant to enhance survival, function, and integrity of the graft. The donor organ is perfused with a SCGB preparation corresponding to a SCGB that is normally expressed by that organ, with or without inclusion of a SCGB1A1 preparation. It is preferable to perfuse the donor organ with the SCGB preparation while the donor is still alive or as soon as possible after the death of the donor and prior to its extraction from the body in order to minimize the trauma associated with transient ischemia, severing of nearby tissues and attached blood vessels, and physical manipulation of the donor organ; events that result in O2/CO2 imbalance, shear stresses, and inflammatory responses sensed by the EG and VECs and trigger EG shedding. The tissue-specific SCGB preparation or SCGB1A1 preparation, or both, is/are also administered intravenously to the recipient within 24 hours, but preferably no more than 2 hours, prior to transplantation; and is also administered after the transplant daily for up to 7 days. For example, SCGB1A1 and SCGB3A2 are highly expressed in lung and either a SCGB1A1 or SCGB3A2 preparation, or combination of both, would be used to prepare a donor lung and to treat the lung transplant recipient. Another example is SCGB1D4, which is thought to be expressed predominantly in heart tissue and a SCGB1D4 preparation is used to prepare a donor heart and to treat a heart transplant recipient. The dose of the SCGB preparation used to perfuse the donor or donor organ prior to removal from the donor or culture, as well as that administered to the recipient, is between 20 ng/kg and 20 mg/kg, but preferably 1-20 mg/kg, preferably administered as an intravenous infusion prior to excision. The donor tissue may also be immersed in, or the surfaces flushed with, a solution containing the SCGB preparation in the same concentration during the time period between excision from the donor or culture and transplant into the recipient. The transplanted tissue containing intact EG, EpiG, and LG is less prone to developing primary graft dysfunction. The method of preventing EG, EpiG, and/or LG shedding in a transplant may be used for any type of tissue or organ, including but not limited to heart, lung, kidney, liver, limb (hand, finger, arm, foot, etc.), eye, ear, face, skin and cultured skin, uterus, bladder and cultured bladder, bone marrow, platelets, red blood cells, and whole blood, or any other organ or tissue intended for transplant.

Example 7: Prevention and treatment of EG shedding due to trauma and/or surgery. Sheer forces and severed blood vessels, blood loss and bruising, and transient ischemia occur during trauma and surgery and result in shedding of EG in the affected tissues. Extensive EG shedding, as measured by increases in circulating shed SDC1 or other HSPGs, is associated with greater complications and poorer clinical outcomes. For example, a car accident victim is rushed to the hospital for emergency surgery to repair a bruised heart and punctured lung. The SCGB1A1 preparation of Example 5 is administered to the victim as soon as possible after the accident and prior to surgery. The dose of the SCGB1A1 preparation that is administered intravenously to prevent or reduce EG shedding in the heart and lungs is between 20 ng/kg and 20 mg/kg, more specifically 1-20 mg/kg/day, for up to 7 consecutive days. The SCGB preparation binds to SDC1, SDC4, GPC3, and/or other HSPGs located in the EG of the lungs and heart, blocking degradation and shedding of the HSPGs from the EG. The maintenance of the integrity of the EG minimizes the increase in vascular permeability and inflammation, thereby avoiding shock and acute lung injury, enabling the victim to survive and to exit the hospital and return to normal activities sooner.

While it is apparent that the invention herein disclosed is well calculated to fulfill the objects above stated, it will be appreciated that numerous modifications and embodiments may be devised by those skilled in the art. It is intended that the appended claims cover all such modifications and embodiments as fall within the true spirit and scope of the present invention.

The invention claimed is:

1. A method of use of a SCGB1A1 preparation composition, comprising the step of (a) administering said preparation to a subject having one or more of the following conditions:
   prior or concurrent severe trauma, or undergoing or about to undergo surgery or after surgery.

2. The method of claim 1 wherein the SCGB1A1 is covalently linked to a lipid.

3. The method of claim 2, wherein the lipid is dipalmitoyl phosphatidylcholine.

* * * * *